United States Patent [19]

Hamminga et al.

[11] Patent Number: 5,100,884
[45] Date of Patent: Mar. 31, 1992

[54] 8,9-ANEALLATED-1,2,3,4-TETRAHYDRO-BETA-CARBOLINE DERIVATIVES

[75] Inventors: Derk Hamminga; Ineke Van Wigngaarden; Johannes W. C. M. Jansen, all of Weesp, Netherlands

[73] Assignee: Duphar International Research B.V., Weesp, Netherlands

[21] Appl. No.: 428,481

[22] Filed: Oct. 30, 1989

Related U.S. Application Data

[63] Continuation of Ser. No. 219,362, Jul. 15, 1988, abandoned.

[30] Foreign Application Priority Data

Jul. 20, 1987 [NL] Netherlands ............... 8701709

[51] Int. Cl.⁵ ............... C07D 487/14; C07D 487/16; A61K 31/33
[52] U.S. Cl. ............... 514/183; 540/477
[58] Field of Search ............... 540/477; 514/183

[56] References Cited

U.S. PATENT DOCUMENTS 3,299,078 1/1967 Pachter ............... 546/67

FOREIGN PATENT DOCUMENTS 0017727 2/1980 European Pat. Off. ............... 546/86
0190472 12/1985 European Pat. Off. ............... 544/376

*Primary Examiner*—Alan L. Rotman
*Attorney, Agent, or Firm*—Stevens, Davis, Miller & Mosher

[57] ABSTRACT

The invention relates to new 8,9-annelated-1,2,3,4-tetrahydro-$\beta$-carboline derivatives of the formula

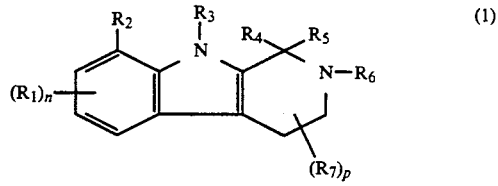

wherein the symbols have the following meanings:

$R_1$ is hydrogen, straight or branched alkyl having 1-6 C-atoms, fluorinated or hydroxylated alkyl having 1-6 C-atoms;

$R_2 + R_3$ together with the carbon atom and the nitrogen atom to which they are bonded and the intermediate carbon atom constitute a hetrocyclic group consisting of 8 ring atoms;

$R_4$ is hydrogen, straight or branched alkyl having 1-8 C-atoms, alkoxy- or alkylthioalkyl having 2-6 C-atoms, alkenyl or alkynyl having 2-8 C-atoms, which groups may be substituted with one or more fluorine atoms or hydroxy groups, or with one phenyl group containing 0-3 groups $R_{10}$, or cycloalkyl group having 3-7 C-atoms, or $R_4$ is cycloalkyl having 3-8 C-atoms which may be substituted with one or more fluorine atoms, alkyl groups having 1-4 C-atoms, cycloalkyl groups having 3-5 C-atoms, or $R_4$ is cycloalkenyl having 5-7 C-atoms which may be substituted with 1-4 methyl groups;

$R_5$ is hydrogen or straight or branched alkyl having 1-6 C-atoms; or $R_6$ is hydrogen, straight or branched alkyl having 1-6 C-atoms which may be substituted with one or more hydroxyl groups or with one optionally substituted phenyl group or alkoxycarbonyl group having 1-3 C-atoms in the alkoxy group, or $R_6$ is a straight or branched alkenyl or alkynyl having 2-6 C-atoms, or a group —CO—X, wherein X is straight or branched alkyl, alkenyl, alkynyl or alkoxy having 1-6 C-atoms, or an optionally substituted phenyl group, or $R_6$ is an amino acid radical of the formula —CO—CHR$_{13}$—NH—R$_{14}$, wherein $R_{13}$ is alkyl and $R_{14}$ is hydrogen, alkanoyl or alkoxycarbonyl having 1-4 C-atoms;

$R_7$ is alkyl having 1-3 C-atoms, or one group $R_7$ is an alkoxycarbonyl group having 1-3 C-atoms in the alkoxy group, or the hydroxymethyl group; and p has the value 0-4, and the salts and prodrugs thereof.

It has been found that these compounds have good fibrinolytic properties and may be used as orally active fibrinolytics.

3 Claims, No Drawings

8,9-ANEALLATED-1,2,3,4-TETRAHYDRO-BETA-CARBOLINE DERIVATIVES

This application is a continuation of application Ser. No. 219,362, filed July 15, 1988 now abandoned.

The invention relates to a group of new 8,9-anellated-1,2,3,4-tetrahydro-$\beta$-carboline derivatives and salts and prodrugs thereof, to the preparation of these compounds and to pharmaceutical compositions which comprise at least one of these compounds as an active substance.

It has been found surprisingly that the compounds of formula 1

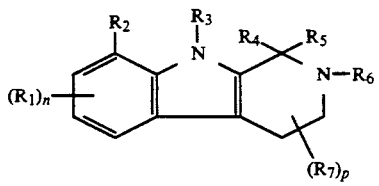

and the salts and prodrugs thereof have good fibrinolytic properties, and in particular may be used as orally active fibrinolytics.

The symbols in the above formula 1 have the following meanings:

$R_1$ is straight or branched alkyl having 1-6 C-atoms, fluorinated or hydroxylated alkyl having 1-6 C-atoms, phenylalkyl having 1-6 C-atoms in the alkyl group, the phenyl group of which may optionally be substituted, or two alkyl groups $R_1$ bonded to adjacent carbon atoms together constitute a ring of 5-7 carbon atoms, which ring may be substituted with alkyl groups having 1-3 C-atoms, or $R_1$ is straight or branched alkenyl or alkynyl having 2-6 C-atoms, which groups may comprise one or more fluorine atoms, or cycloalkyl having 3-6 C-atoms which are substituted with 0-4 methyl groups, or $R_1$ is straight or branched alkoxy or alkylthio having 1-6 C-atoms which may be substituted with one or more fluorine atoms or hydroxyl groups, or with one optionally substituted phenyl group, or two alkoxy groups and/or alkylthio groups bonded to two adjacent carbon atoms may form a ring consisting of 5-7 ring atoms which may be substituted with hydroxymethyl, alkoxy or alkoxyalkyl groups having 1-6 C-atoms, or $R_1$ is a cycloalkoxy group or cycloalkylthio group having 3-6 C-atoms which may be substituted with 1-4 methyl groups, or $R_1$ is straight or branced alkoxy-, alkylthio-, or alkylsulponylakyl having 2-6 C-atoms which may comprise one or more fluorine atoms or hydroxyl groups, or $R_1$ is an alkoxycarbonylmethyl group having 1-6 C-atoms in the alkoxy group, or $R_1$ is a group $R_8R_9N$—CO—CH$_2$—, $R_8R_9N$—CO— or $R_8R_9N$—SO$_2$ wherein $R_8$ and $R_9$ independently of each other are hydrogen, alkyl having 1-3 C-atoms, or, together with the nitrogen atom, form a heterocyclic 5- or 6-ring, or $R_1$ is hydroxy, halogen, cyano, straight or branched alkoxycarbonyl having 1-6 C-atoms in the alkoxy group, cycloalkylsulphonyl having 3-8 C-atoms which may be substituted with 1-4 methyl groups;

n has the value 0-3;

$R_2+R_3$ together with the carbon atom and the nitrogen atom to which they are bonded and the intermediate carbon atom constitute a heterocyclic group consisting of 5-8 ring atoms which, in addition to the nitrogen atom already present, may comprise a second hetero atom from the group N, O, S, S—O or SO$_2$, and which may be substituted with 1-3 alkyl groups having 1-4 C-atoms, which can form a spiroalkyl group having 2-5 C-atoms, or the hetero group may be substituted with a phenyl group comprising 0-3 groups $R_{10}$, wherein $R_{10}$ is alkyl or alkoxy having 1-3 C-atoms, halogen, trifluoromethyl, cyano or hydroxy and two alkyl groups or alkoxy groups $R_{10}$ bonded to adjacent carbon atoms may form a ring annellated with the phenyl group and consisting of 5-7 ring atoms, which ring may be substituted with alkyl or alkoxy having 1-3 C-atoms, or with akoxyalkyl having 1-6 C-atoms, and the ring formed by $R_2+R_3$ may be annellated with a saturated or unsaturated carbocyclic or heterocyclic ring consisting of 5- or 6-ring atoms which may be substituted with halogen or alkyl having 1-4 C-atoms;

$R_4$ is hydrogen, straight or branched alkyl having 1-8 C-atoms, alkoxy- or alkylthioalkyl having 2-6 C-atoms, alkenyl or alkynyl having 2-8 C-atoms, which groups may be substituted with one or more fluorine atoms or hydroxy groups, or with one phyenyl group containing 0-3 groups $R_{10}$, or cycloalkyl group having 3-7 C-atoms, or $R_4$ is cycloalkyl having 3-8 C-atoms which may be substituted with one or more fluorine atoms, alkyl groups having 1-4 C-atoms, cycloalkyl groups having 3-5 C-atoms, or $R_4$ is cycloalkenyl having 5-7 C-atoms which may be substituted with 1-4 methyl groups, or $R_4$ is straight or branched alkoxycarbonylalkyl having 0-6 C-atoms in the alkoxy group and 1-3 C-atoms in the alkyl group, or $R_4$ is a group $R_8R_9N$—CO—$R_{11}$— or $R_8R_9N$—SO$_2$—$R_{11}$—, wherein $R_8$ and $R_9$ have the above-mentioned meanings and $R_{11}$ is alkyl having 1-3 C-atoms, or $R_4$ is alkylsulphonylalkyl having 1-3 C-atoms per alkyl group, or a phenylsulphonylalkyl group having 1-3 C-atoms in the alkyl group and the phenyl group comprises 0-3 groups $R_{10}$, or $R_4$ is a phenyl group substituted with 0-4 groups $R_{12}$, wherein $R_{12}$ is straight or branched alkyl having 1-6 C-atoms which may be susbstituted with one or more fluorine atoms or hydroxyl groups, or with one cyano group, or with straight or branched alkoxycarbonyl having 0-6 C-atoms in the alkoxy group, or with a group $R_8R_9N$—CO— or $R_8R_9N$—SO$_2$—, wherein $R_8$ and $R_9$ have the above-mentioned meanings, or two groups $R_{12}$ bonded to adjacent carbon atoms form a ring anellated with the phenyl group and consisting of 5-7 ring atoms, which ring may be substituted with 1-3 alkyl groups having 1-3 C-atoms, or $R_{12}$ is straight or branched alkyl (1-4 C)oxy-alkyl(0-3 C), alkyl (1-4 C)-thio-alkyl(0-3 C) or alkyl(1-4 C)-sulphonylalkyl(0-3 C) which groups may comprise one or more fluorine atoms or hydroxyl groups, or of which two alkoxy groups or alkylthio groups bonded to adjacent carbon atoms form a ring which consists of 5-7 ring atoms and may be substituted with alkyl or alkoxy having 1-3 C-atoms, or with hydroxymethyl, or with alkoxyalkyl having 2-6 C-atoms, or $R_{12}$ is cycloalkoxy or cycloalkylthio having 3-7 C-atoms which may be substituted with 0-4 methyl groups, or $R_{12}$ is cycloalkyl having 3-7 C-atoms in which one ore more fluorine atoms or methyl groups may be present, or $R_{12}$ is straight or branched alkoxycarbonyl having 1-6 C-atoms in the alkoxy group, a groups $R_8R_9N$—CO— or $R_8R_9N$—SO$_2$— wherein $R_8$ and $R_9$ have the above-mentioned meanings, or $R_{12}$ is halogen or hydroxy, or $R_4$ is mono- or bicyclic heteroaryl group in which N and/or O and/or S may be present as hetero atoms, and the ring(s) may be substituted with alkyl, alkoxy or alkylthio having 1-3 C-atoms, halogen, keto oxygen atom, cyano and/or $CF_3$;

$R_5$ is hydrogen or straight or branched alkyl having 1-6 C-atoms; or $R_4 + R_5$, together with the carbon atom to which they are bonded, may form a carbocyclic or heterocyclic ring consisting of 5-7 ring atoms which may comprise N, O, S, SO or $SO_2$ as a hetero atom;

$R_6$ is hydrogen, straight or branched alkyl having 1-6 C-atoms which may be substituted with one or more hydroxyl groups or with one optionally substituted phenyl group or alkoxycarbonyl group having 1-3 C-atoms in the alkoxy group, or $R_6$ is a straight or branched alkenyl or alkynyl having 2-6 C-atoms, or a group —CO—X, wherein X is straight or branched alkyl, alkenyl, alkynyl or alkoxy having 1-6 C-atoms, or an optionally substituted phenyl group, or $R_6$ is an amino acid radical of the formula —CO—$CHR_{13}$—NH—$R_{14}$, wherein $R_{13}$ is alkyl and $R_{14}$ is hydrogen, alkanoyl or alkoxycarbonyl having 1-4 C-atoms;

$R_7$ is alkyl having 1-3 C-atoms, or one group $R_7$ is an alkoxycarbonyl group having 1-3 C-atoms in the alkoxy group, or the hydroxymethyl group; and p has the value 0-4.

Suitable acids with which the compounds of formula 1 according to the invention can form pharmaceutically acceptable acid addition salts are, for example, hydrochloric acid, sulphuric acid, phosphoric acid, nitric acid, and organic acids, for example, citric acid, fumaric acid, maleic acid, tartaric acid, acetic acied, benzoic acid, p-toluene sulphonic acid, methane sulphonic acid, and the like.

When the symbols $R_4$ and $R_5$ have different meanings and/or when p has the value 1, 2 or 3 and/or when $R_2$ and $R_3$, together with the carbon atoms and nitrogen atom, respectively, to which they are bonded and the intermediate carbon atom form a ring which is substituted, the compounds of formula 1 comprise one or more chiral centres. The invention relates both to racemates and individual enantiomers.

The invention also relates to prodrugs of the compounds of formula 1, i.e. derivatives of these compounds which as such are inactive, from which, after splitting off of an easily removable group, for example an ester group or an ether group, an active compound of formula 1 is obtained.

The carboline derivatives according to the invention are orally active fibrinolytics and may hence be used in the control of already formed venous or arterial thrombi or may be administered to prevent thrombi. The compounds may be used, for example, for a short period of time in operations, or for long periods in the case of enhanced risk after, for example, myocard infarct, cerebral or peripheral suffering. The best compounds probably are active via an increase of the tissue plasminogen activator activity as a result of which the possibility of spontaneous bleedings can be prevented.

The compounds according to the invention are fibrinolytically active in oral doses of less than 50 mg/kg.

The oral fibrinolytic activity of the compounds according to the invention was established first of all in rats in the so-called DBCLT (Diluted Blood Clot Lysis Test; Taylor F. B. et al, Fed. Proc. (1981), 40 (2092-2098). Rats are treated orally with the test compound. After 1-3 hours blood is taken. $^{125}I$-labelled fibrinogen and thrombine are added so that a blood clot is formed which, depending on the extend of fibrinolytic activity caused by the test compound dissolves more rapidly as compared with blood clots of untreated animals.

The increase of tissue plasminogen activator activity was measured in cultures of endothelinm cells (Thrombosis Diathesis Haemorrhagis (Stuttgart), 34, (1975), pp. 825-839; and Thrombosis and Haemostasis, 51, (1984), p.392).

Concentrations of less than 10 μmol per liter of the compounds give a good increase of the plasminogen activator activity.

The pharmacologically active compounds falling within the scope of the present invention, their prodrugs and salts can be brought into forms suitable for administration, for example, pills, tablets, coated tablets, capsules, powders, injection liquids, and the like, by means of techniques suitable for this purpose and while using suitable auxiliary substances, for example, solid or liquid carrier materials.

The dosage in which the compounds according to the invention may be used depend on the severity and the nature of the disease to be treated and on the way of administration.

The dosage in which the compounds according to the invention may be used depend on the severity and the nature of the disease to be treated and on the way of administration.

The compounds of formula 1, dependently of the meanings of the symbols, may be prepared in at least one of the following manners.

a) analogously to the method described in Advances in Heterocyclic Chemistry, Vol. 3 pp. 79-207 (The Carbolines). More in particular, compounds of this type can be obtained in a good yield by reaction of a compound of formula 2 .

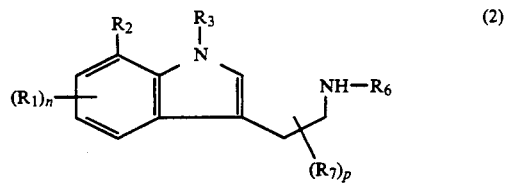

(2)

wherein $R_1$-$R_3$, n, p, $R_6$ and $R_7$ have the above-mentioned meanings, or a salt thereof, with a carbonyl compound of formula 3

(3)

wherein $R_4$ and $R_5$ have the above-mentioned meanings. The reaction is preferably carried out in a suitable solvent, for example, acetic acid, alcohol, etc., at a temperature between 10° and 120° C.

The starting compounds of formula 2 necessary for this mode of preparation can be obtained in a manner known for the synthesis of analogous compounds, for example, by reaction of a compound of formula 4

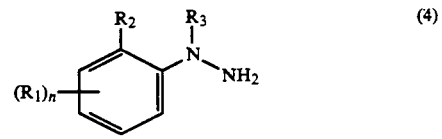

(4)

with a compound of formula 5 or 6

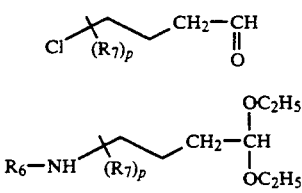

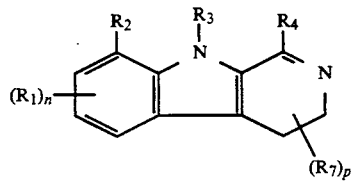

in which formulae $R_1$–$R_7$, n and p have the above-mentioned meanings (see also Khimiya Geterotsiklicheskikh Soedineii, (1973), pp. 213–218 and J. Heterocyclic Chem. 11, (1974), pp. 387–393).

b) The compounds of formula 1 can also be obtained by reduction of a compound having formula 7

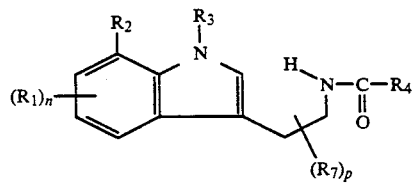

wherein $R_1$,n, $R_2$, $R_3$, $R_4$, $R_7$ and p have the above meanings with a suitable reducing agent, for example hydrogen and a catalyst.

The starting compounds of formula 7 can be obtained in good yield by means of the Bischler-Napieralsky ringclosure of a compound of the formula 8 wherein the symbols have the above given meanings. Suitable methods for this Bischler-Napieralsky reaction are described in Organic Reactions, vol. VI, page 74.

The compounds of formula 1 in which $R_6$ has a meaning other than hydrogen, can also be obtained by reacting the analogous compound wherein $R_6$=H, in known manner with a compound $R_6$-Y, wherein Y is a reactive group, for example, halogen, ethoxycarbonyloxy, or acetoxy.

The invention will now be described in greater detail with reference to the ensuring specific examples.

EXAMPLE I (R,S)-1-Cyclohexyl-1,2,3,4,9,10,11,12-octahydro-8H-pyrido[4′,3,′:4,5]-pyrrolo-[3,2,1-kl]-[1]-benzazocine hydrochloride.

a) 26.8 g (0.152 mol) of 1-amino-1,2,3,4,5,6-hexahydro-[1]-benzazocine were dissolved in a mixture of 400 ml of methanol and 40 ml of water, and the solution was heated to boiling. 17.8 g (0.167 mol) of 4-chlorobutanal were added carefully and the mixture was refluxed for 20 hours. The reaction mixture was then evaporated in vacuo and the residue was extraced with a mixture of methylene chloride and 2N sodium hydroxide. The organic layer was washed with water and evaporated in vacuo. The residue was purified by means of flash-chromatography on silicageel, using methylene chloride, methanol and ammonia (92.5:7:0.5) as an eluent. Yield 25.5 g (73%) of 1-(2-amino-ethyl)-5,6,7,8-tetrahydro-4H-pyrrolo-[3,2,1-kl]-[1]-benzazocine.

b) 30 g (0.132 mol) of 1-(2-amino-ethyl)-5,6,7,8-tetrahydro-4H-pyrrolo-[3,2,1-kl]-[1]-benzazocine were dissolved in 500 ml of acetic acid. 16.2 g (0.144 mol) of cyclohexane carboxaldehyde were added and the mixture was stirred at 40° C. for 70 hours. The mixture was then poured out on ice, made basic with 50% sodium hydroxide, and extracted with methylene chloride. The methylene chloride solution was washed with water and evaporated. The residue was purified by means of chromatography on silicagel using methylene chloride/methanol/ammonia (92.5:7:0.5) as an eluent. Yield 28 g (66%) of (R,S)-1-cyclohexyl-1,2,3,4,9,10,11,12-octahydro-8H-pyrido-[4′,3′:4,5]-pyrrolo]3,2,1-kl]-[1]-benzazocine.

The free base was dissolved in ethyl acetate and 1 equivalent of hydrochloric acid in ethanol was added. The solid substance was sucked off, washed and dried. The so-obtained hydrochloride had a melting point of 270.5°–271° C.

The compounds of formula 1 in table A hereinafter were obtained according to the methods of Example I:

TABLE A

| no. | $(R_1)_n$ | $R_2 + R_3$ | $R_4$ | $R_5$ | $R_6$ | $(R_7)_p$ | salt | m.p. °C. |
|---|---|---|---|---|---|---|---|---|
| 1 | 5-Cl | —$CH_2CH_2$— | cyclo-$C_6H_{11}$ | H | H | H | HCl | 268–271 |
| 2 | 6-Cl | —$CH_2CH_2$— | cyclo-$C_6H_{11}$ | H | H | H | base | 82–83 |
| 3 | 7-Cl | —$CH_2CH_2$— | benzyl | H | H | H | HCl | 237–238 |
| 4 | 7-Cl | —$CH_2CH_2$— | $H_2C$=CF— | H | H | H | HCl | 105–110 |
| 5 | H | —$(CH_2)_3$— | cyclo-$C_5H_9$ | H | H | H | HCl | 265.5–267.5 |
| 6 | H | —$(CH_2)_3$— | phenyl | H | H | 10-COO$C_2H_5$ | base* | 104–110 |
| 7 | H | —$(CH_2)_3$— | cyclo-$C_8H_{15}$ | H | H | H | HCl | 252.5–253 |
| 8 | H | —$(CH_2)_3$— | 4-$CH_3$-phenyl | H | H | H | HCl | 280–283 |
| 9 | H | —$(CH_2)_3$— | 4-$(CH_3)_2$CH-phenyl | H | H | H | HCl | 255–257 |
| 10 | H | —$(CH_2)_3$— | 4-$(CH_3)_2$CHO-phenyl | H | H | H | HCl | 178–180 |
| 11 | H | —C$(CH_3)_2$—$(CH_2)_2$— | cyclo-$C_6H_{11}$ | H | H | H | HCl | 281–283 |
| 12 | H | —C$(CH_3)_2$—$(CH_2)_2$— | phenyl | H | H | H | HCl | 285–287 |
| 13 | H | —C$(CH_3)_2$—$(CH_2)_2$— | 4-$CH_3$-phenyl | H | H | H | HCl | 272–285 |
| 14 | H | —C$(CH_3)_2$—$(CH_2)_2$— | $H_2C$=CF— | H | H | H | HCl | 249–251 (decomp) |
| 15 | H | —C$(C_2H_5)_2$—$(CH_2)_2$— | phenyl | H | H | H | HCl | 275–277 |
| 16 | H | —C$(C_2H_5)_2$—$(CH_2)_2$— | 4-$CH_3$-phenyl | H | H | H | HCl | 273–274 |
| 17 | H | —C$(CH_3)_2$— | —$CH_2$—$CH_2$—$CH_2$—$CH_2$—$CH_2$ | H | H | H | HCl | 254–257 |

TABLE A-continued

| no. | $(R_1)_n$ | $R_2 + R_3$ | $R_4$ | $R_5$ | $R_6$ | $(R_7)_p$ | salt | m.p. °C. |
|---|---|---|---|---|---|---|---|---|
| 18 | 5-Br | —(CH$_2$)$_3$— | H | H | CH$_3$ | H | base | 106–108 |
| 19 | 5-Br | —(CH$_2$)$_3$— | 4-CH$_3$-phenyl | H | H | H | HCl | 307–310 |
| 20 | 5-CF$_3$ | —(CH$_2$)$_3$— | 4-CH$_3$-phenyl | H | H | H | HCl | 290.5–291.5 |
| 21 | 5-CF$_3$ | —(CH$_2$)$_3$— | 4-CH$_3$O-phenyl | H | H | H | HCl | 286–288 |
| 22 | 5-CF$_3$ | —(CH$_2$)$_3$— | 4-HCF$_2$—CF$_2$—O-phenyl | H | H | H | HCl | 281–281.5 |
| 23 | 6-F | —(CH$_2$)$_3$— | phenyl | H | H | H | HCl | 274–276.5 |
| 24 | 6-F | —(CH$_2$)$_3$— | 4-CH$_3$-phenyl | H | H | H | HCl | 267 (decomp) |
| 25 | 6-Cl | —(CH$_2$)$_3$— | H$_2$C=CF— | H | H | H | HCl | 145 (decomp) |
| 26 | 6-Cl | —(CH$_2$)$_3$— | phenyl | H | H | H | HCl | 295–297 |
| 27 | 6-Cl | —(CH$_2$)$_3$— | phenyl | H | CH$_3$—C=O | H | base | foam |
| 28 | 6-Cl | —(CH$_2$)$_3$— | phenyl | H | C$_2$H$_5$—O—C=O | H | base | 193–195 |
| 29 | 6-Cl | —(CH$_2$)$_3$— | 2-F-phenyl | H | H | H | HCl | 305–307 |
| 30 | 6-Cl | —(CH$_2$)$_3$— | 2-Cl-phenyl | H | H | H | HCl | 317–318 |
| 31 | 6-Cl | —(CH$_2$)$_3$— | 4-CH$_3$-phenyl | H | H | H | HCl | 275–278 |
| 32 | 6-Cl | —(CH$_2$)$_3$— | 4-CH$_3$CH$_2$-phenyl | H | H | H | HCl | 258–262 |
| 33 | 6-Cl | —(CH$_2$)$_3$— | 4-(CH$_3$)$_2$CH—O-phenyl | H | H | H | HCl | 275–280 |
| 34 | 6-Cl | —(CH$_2$)$_3$— | 4-HCF$_2$—CF$_2$—O-phenyl | H | H | H | HCl | 287–289 |
| 35 | 6-Cl | —C(CH$_3$)$_2$—(CH$_2$)$_2$— | cyclohexyl | H | H | H | HCl | 269–270 |
| 36 | 6-Cl | —C(CH$_3$)$_2$—(CH$_2$)$_2$— | phenyl | H | H | H | HCl | 280–281 |
| 37 | 6-Cl | —C(CH$_3$)$_2$—(CH$_2$)$_2$— | 4-CH$_3$-phenyl | H | H | H | base | 104–105 |
| 38 | 6-CH$_3$ | —(CH$_2$)$_3$— | phenyl | H | H | H | HCl | 287–289 |
| 39 | 6-CH$_3$ | —(CH$_2$)$_3$— | 4-CH$_3$-phenyl | H | H | H | HCl | 291–295 |
| 40 | 6-CH$_3$ | —C(CH$_3$)$_2$—(CH$_2$)$_2$— | 4-CH$_3$-phenyl | H | H | H | HCl | 278–280 |
| 41 | 6-(CH$_3$)$_2$CH— | —C(CH$_3$)$_2$—(CH$_2$)$_2$— | phenyl | H | H | H | HCl | 200–260 |
| 42 | 6-(CH$_3$)$_2$CH— | —C(CH$_3$)$_2$—(CH$_2$)$_2$— | 4-CH$_3$-phenyl | H | H | H | HCl | 170–210 |
| 43 | 7-F | —(CH$_2$)$_3$— | H | H | H | H | HCl | 279–280 |
| 44 | 7-F | —(CH$_2$)$_3$— | cyclohexyl | H | H | H | HCl | 275–278 |
| 45 | H | —(CH$_2$)$_4$— | 4-CH$_3$-phenyl | H | H | h | HCl | 262–266 |
| 46 | H | —(CH$_2$)$_4$— | 4-CH$_3$-phenyl | CH$_3$—C=O | H | H | base | 79–85 |
| 47 | H | —(CH$_2$)$_4$— | 4-CH$_3$CH$_2$-phenyl | H | H | H | HCl | 278–280 |
| 48 | H | —(CH$_2$)$_4$— | 4-(CH$_3$)$_2$CH-phenyl | H | H | H | HCl | 273–375 |
| 49 | H | —(CH$_2$)$_4$— | 4-(CH$_3$)$_2$N-phenyl | H | H | H | 2HCl | 216–218 |
| 50 | H | —(CH$_2$)$_4$— | 4-HCF$_2$—CF$_2$—O-phenyl | H | H | H | HCl | 241–242.2 |
| 51 | H | —(CH$_2$)$_4$— | 2,4-diCH$_3$-phenyl | H | H | H | HCl | 266.8–270.2 |
| 52 | H | —(CH$_2$)$_4$— | 3,5-diCH$_3$-4-CH$_3$O--phenyl | H | H | H | HCl | 278–281 |
| 53 | H | —(CH$_2$)$_4$— | H$_2$C=CF— | H | H | H | HCl | 222–225 |
| 54 | 6-CH$_3$ | —(CH$_2$)$_4$— | phenyl | H | H | H | base | oil |
| 55 | 6-CH$_3$ | —(CH$_2$)$_4$— | 4-CH$_3$-phenyl | H | H | H | base | oil |
| 56 | H | —(CH$_2$)$_5$— | 4-CH$_3$-phenyl | H | H | H | HCl | 267.5–270.5 |
| 57 | H | —(CH$_2$)$_5$— | 4-CF$_3$ | H | H | H | HCl | 216–217 |
| 58 | H | —(CH$_2$)$_5$— | cyclopentyl | H | H | H | HCl | 271–272 |
| 59 | H | —(CH$_2$)$_5$— | isopropyl | H | H | H | HCl | 253–254 |
| 60 | H | —(CH$_2$)$_5$— | H$_2$C=CF— | H | H | H | HCl | 223–224 |

*mixture of cis:trans of 4:1

EXAMPLE II (R,S)-8-Cyclohexyl-5,6,8,9,10,11-hexahydro-4H-pyrido-[4',3':4,5]-pyrrolo-[3,2,1,-ij]-quinoline hydrochloride.

a) 0.5 g (1.61 mmol) of 1-[2-(cyclohexyl-carbox-amide)ethyl]-5,6-dihydro-4H-pyrrolo-[3,2,1-ij]-quinoline were mixed with 6 ml of phosphoroxy chloride and stirred for 1 hour at 105° C. The excess of phosphoroxy chloride was then distilled off in cacuo. The residue was extracted with methylene chloride and excess of 2N sodium hydroxide. The organic layer was dried and evaporated in vacuo. The residue was dissolved in ethyl acetate, and 1.1 equivalent of hydrochloric acid in ethanol was added. The solid substance was sucked off, washed with ethyl acetate and dried. Yield 0.45 g (85%) of 8-cyclohexyl-5,6,10,11-tetrahydro-4H-pyrido-[4',3':4,5]-pyrrolo-[3,2,1-ij]quinoline hydrochloride having a melting point of 193°–195° C.

b) 0.45 g (1.37 mmol) of the hydrochloride compound obtained in a) were dissolved in 30 ml of methanol and hydrogenated with platinum as a catalyst at room temperature. After 30 min. of hydrogenating the reaction mixture was sucked off. The filtrate was evaporated in vacuo. The residue was washed with ethyl acetate and dried. Yield: 0.44 g (97%) of (R,S)-8-cyclohyxyl-5,6,8,9,10,11-hexahydro-4H-pyrido-[4',3':4,5]-pyrrolo-[3,2,1-ij]quinoline hydrochloride having a melting point of 273°–275° C.

In an analogous way the following compound was obtained: (R,S)-1-cycloheptyl-1,2,3,4,9,10,11,12-octahydro-8H-pyrido-[4',3';4,5]-pyrrolo-[3,2,1-kl]-benzazocine hydrochloride; melting point 258°–258.5° C.

EXAMPLE III

2-Chloro-9-ethoxycarbonyl-8-phenyl-5,6,8,9,10,11-hexahydro-4H-pyrido-[4',3':4,5]-pyrrolo-3,2,1-ij]-quinolinehydrochoride.

2.26 g (7 mmol) Of 2-chloro-8-phenyl-5,6,8,9,10,11-hexahydro-4H-pyrido-[4',3':4,5]-pyrrolo-[3,2,1-ij]quinoline were dissolved in 30 ml of methylene chloride. 0.95 ml Of triethylamine and 0.66 ml of chloroformic acid ethyl ester were added successively at 20° C. and the mixture was stirred at 20° C. for two hours. The mixture was then washed with 2N hydrochloric acid and the organic layer was evaporated in vacuo. The residue was chromatographed over silicagel using methanol/methylene chloride 3:97 as an eluent.

Yield 2.3 g (=93%), melting-point 193°–195° C.

EXAMPLE IV (−)-1-Cyclohexyl-1,2,3,4,9,10,11,12-octahydro-4H-pyrido [4',3':4,5]-pyrrolo-[3,2,1-kl]-[1]-benzazocine hydrochloride.

8.0 g (0.025 mol) (R,S)-1-cyclohexyl-1,2,3,4,9,10,11,12-octahydro-8H-pyrido-[4',3':4,5]-pyrrolo-[3,2,1-kl]-[1]benzazocine were dissolved in 240 ml of warm methyl ethyl ketone. 4.35 g (0.015 mol) of (−)-diacetone-2-keto-L-gulonic acid, dissolved in 60 ml of warm methyl ethyl ketone, were added and the mixture was cooled. The solid substance was sucked off after a few hours, washed with little methyl ethyl ketone and dried. The obtained salt was extracted with excess of 2N sodium hydroxide and methylene chloride. The organic layer was evaporated in vacuo. The residue was dissolved in 150 ml of warm methyl ethyl ketone. A solution of 2.95 g (0.01 mol) of (−)-diacetone-2-keto-L-gulonic acid in 50 ml of warm methyl ethyl ketone was added, the mixture was cooled, and after a few hours it was sucked off, washed and dried. The obtained salt was extracted with 2N sodium hydroxide and methylene chloride. The organic layer was dried and evaporated in vacuo. The residue was dissolved in ethyl acetate, and 1.1 equivalent of hydrochloric acid in ethanol was added. The solid substance was sucked off, washed with ethyl acetate and dried. Yield: 3.2 g; $[\alpha]^{25}D = -73.3°$ (c=2.0; methanol); melting point: decomposition starts at 240° C. According to HPCL-analysis at least 98% of the product is the levo rotating isomer.

EXAMPLE V (+)-1-Cyclohexyl-1,2,3,4,9,10,11,12-octahydro-8H-pyrido[4',3':4,5]-pyrrolo[3,2,1-kl]-[1]-benzazocine hydrochloride.

The mother liquors obtained in Examples IV after sucking off the (−)-diacetone-2-keto-L-gulonic acid salts were added to each other and evaporated in vacuo. The residue was extracted with 2N sodium hydroxide and methylene chloride, and evaporated in vacuo. The residue was dissolved in 150 ml of warm methyl ethyl ketone. 1.95 g of D(−)-mandelic acid dissolved in 50 ml of warm methyl ethyl ketone were added, and the mixture was left to cool down. After a few hours the mixture was sucked off, washed with methyl ethyl ketone and dried. The obtained salt was extracted with methylene chloride and excess of 2N sodium hydroxide. The organic layer was dried and evaporated in vacuo. The residue was dissolved in ethyl acetate, and 1.1 equivalent of hydrochloric acid in ethanol was added. The solid substance was sucked off, washed with ethyl acetate and dried.

Yield: 3.5 g; $[\alpha]^{25}D = +68.4°$ (C=2.0; methanol). Melting point: decomposition starts at 240° C.

According to HPLC-analysis at least 98% of the product consists of the dextro rotating isomer.

We claim:

1. A compound of the formula

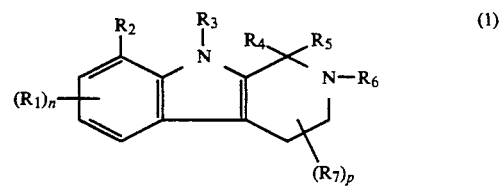

wherein

R$_1$ is hydrogen, straight or branched C$_1$–C$_4$ alkyl, halogen or trifluoromethyl;

n has the value 1;

R$_2$+R$_3$ together with the carbon and the nitrogen to which they are linked and the intermediate carbon form a heterocyclic 8-membered ring, which can be substituted with 1 or 2 C$_1$–C$_2$ alkyl;

R$_4$ is hydrogen, straight or branched C$_1$–C$_4$ alkyl, trifluoromethyl, alkenyl or halogenated alkenyl having 2–4 carbon atoms, C$_3$–C$_6$ cycloalkyl, phenyl, benzyl, tolyl or methoxyphenyl in which groups the phenyl ring can be halogenated;

R$_5$, R$_6$ and R$_7$ are hydrogen; and p has a value of 0–4;

or a pharmaceutically acceptable salt thereof.

2. A pharmaceutical composition having fibrinolytic activity and comprising a fibrinolytically effective amount of at least one compound as claimed in claim 1 as an active substance and a pharmaceutically acceptable carrier.

3. A method of dissolving blood clots, comprising applying a fibrinolytically effective amount of a carboline derivative as claimed in claim 1 to a human patient.

* * * * *